United States Patent [19]

Mena

[11] Patent Number: 5,472,450

[45] Date of Patent: Dec. 5, 1995

[54] MECHANISM FOR SYRINGE NEEDLE DISPOSAL

[76] Inventor: Raul Mena, 201 N. University Dr., Ste. 101, Plantation, Fla. 33324

[21] Appl. No.: 214,771

[22] Filed: Mar. 17, 1994

[51] Int. Cl.⁶ .................................................. A61B 17/00
[52] U.S. Cl. ......................... 606/205; 294/99.2; 606/211
[58] Field of Search ................................. 606/205–211; 294/99.2

[56] References Cited

U.S. PATENT DOCUMENTS

| 5,143,414 | 9/1992 | Rosellini | 254/99.2 |
| 5,156,431 | 10/1992 | Lowe | 606/210 |
| 5,391,181 | 2/1995 | Johnson et al. | 606/207 |

FOREIGN PATENT DOCUMENTS

| 4115548 | 11/1991 | Germany | 606/206 |
| 4017306 | 12/1991 | Germany | 606/205 |
| 4027570 | 3/1992 | Germany | 606/207 |

*Primary Examiner*—Stephen C. Pellegrino
*Assistant Examiner*—William Lewis

[57] ABSTRACT

An improvement for medical and dental instruments of the type that include two handle legs joined by a pivoting joint. The improvement provides for opposite and cooperating curved portions that, when brought towards each other, define a gripping area capable of firmly holding a safety cap or carpule for syringe needles thereby avoiding possible injuries to the user. The internal walls of the curved portions are provided with irregularities or serrations to enhance their gripping function on the carpule. In all instruments, the separation of the curved portions to the area where a user applies the actuating force has been maximized to minimize the likelihood of accidental injury.

3 Claims, 2 Drawing Sheets

5,472,450

MECHANISM FOR SYRINGE NEEDLE DISPOSAL

BACKGROUND OF THE INVENTION

1. Field of the Invention

The present invention relates to dental and medical instruments, and more particularly, to such instruments that include a mechanism for safely handling and disposing of syringe needles.

2. Description of the Related Art

The hazards of handling syringe needles, specially in a dental office environment, has become of great concern to patients and workers alike. Accidental injuries with needles are no longer cured with a bandage but in ever increasing numbers have become vehicles for the transmission of fatal diseases, such as AIDS and hepatitis among others. The problem of handling needles has become worse with the use of gloves since it makes the manipulation of these devices more difficult and little protection is offered by the flexible and vulnerable material of which they are made. Hence a need for instruments that incorporate mechanisms for safely disposing of needles after they are used.

Other patents describing the closest subject matter provide for a number of more or less complicated features that fail to solve the problem in an efficient and economical way. None of these patents suggest the novel features of the present invention.

SUMMARY OF THE INVENTION

It is one of the primary objects of the present invention to provide a mechanism for removing and recap needles from their packages, from a syringe after being used and in other ways manipulating it in a safe manner.

It is another object of the present invention to provide a mechanism that can be adapted to conventional and popular instruments used in dental and medical offices.

It is still another object of this invention to provide a sturdy and reliable mechanism to handle syringe needles to protect a user from being accidentally injured.

It is also an object of this invention to be incorporated on dental and medical instruments commonly found in these professionals' armamentarium.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
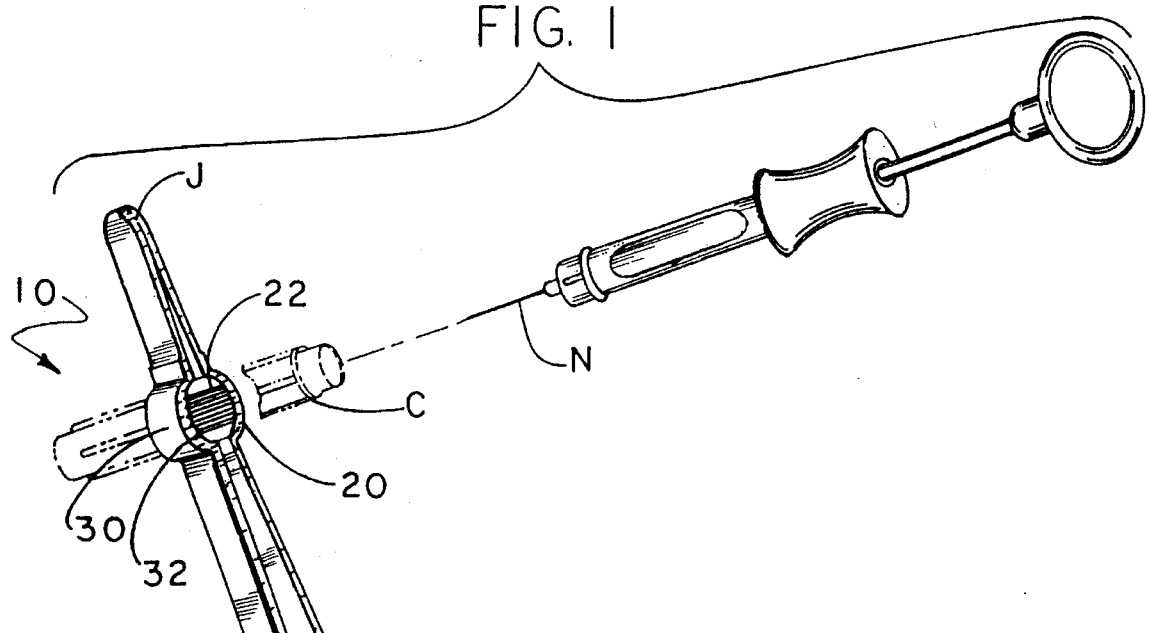
FIG. 1 represents a conventional cotton pliers wherein the mechanism subject of the present invention has been incorporated, and a syringe is represented with a needle mounted thereon and about to be disengaged for its proper and safe disposal.

Referring now to the drawings, where the present invention is generally referred to with numeral 10, it can be observed that it basically includes two opposite curved walls 20 and 30 having each an internal surface that includes friction enhancing irregularities or serrations 22 and 32, respectively. Curved walls 20 and 30 are formed on the handle legs L of common instruments used in medical and dental offices such as college or cotton pliers, scissors and the like. The dimensions and radius of curvature of curved walls 20 and 30 are of such dimensions to cooperatively provide an effective grip for the cylindrical container or tubular member C typically used with syringe needles N.

Figure 2:
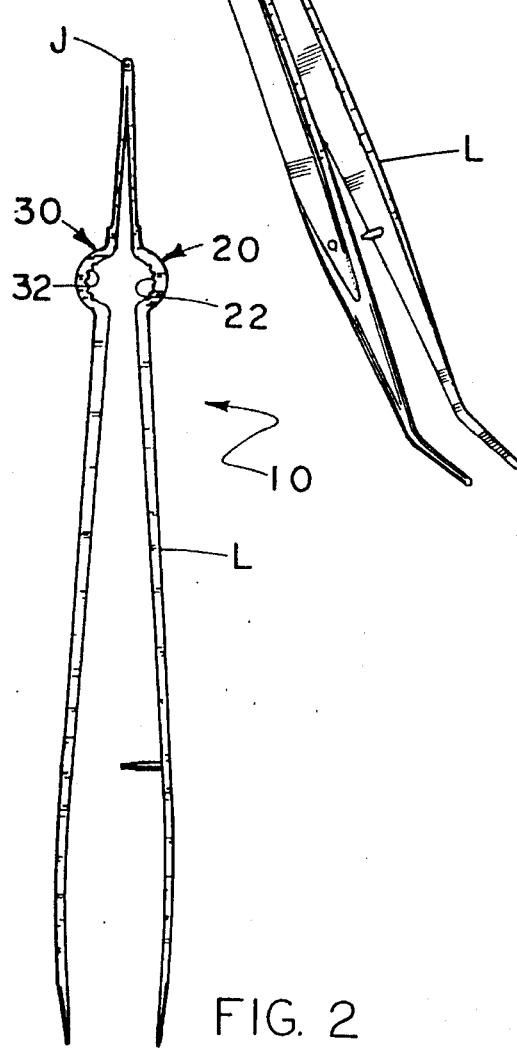
FIG. 2 shows a front elevational view of the device shown in FIG. 1.
Figure 3:
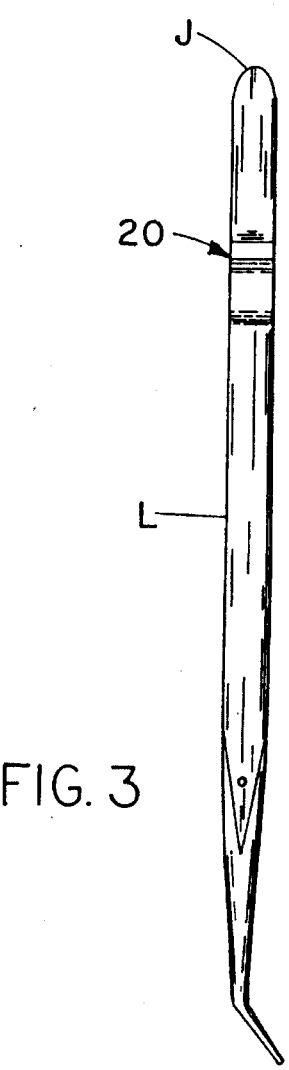
FIG. 3 illustrates is a side elevational view of the device illustrated in the previous two figures.

FIGS. 1 through 3 represent a common cotton pliers with curved walls for 20 and 30 on handle legs L, preferably closed to joint J. The closer to J, the greater the force the user will have available and the farther needle N is from the user, the safer the operation will be.

Figure 4:
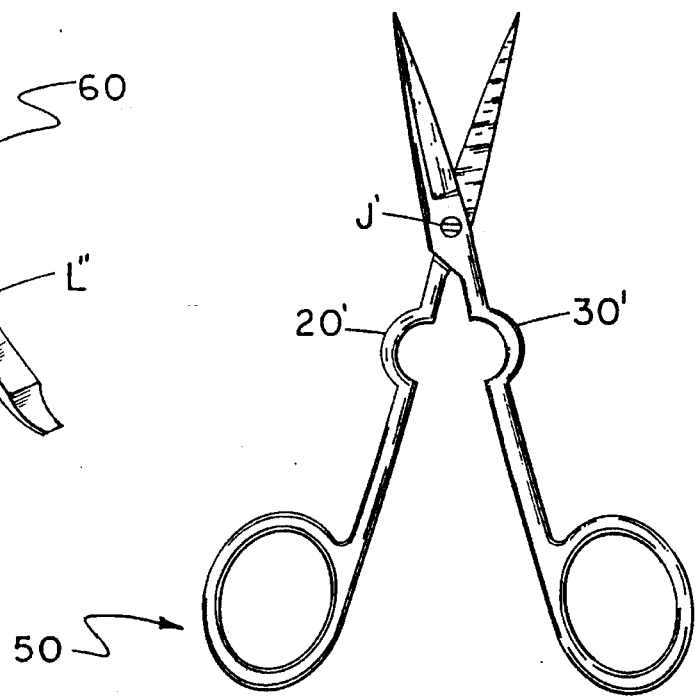
FIG. 4 is a top view of a pair of scissors having the curved portions between the joint and the area where a user applies force to actuate it.

FIG. 4 shows a representation of a pair of scissors 50 with curved walls 20' and 30', similar to those disclosed for the device shown in figures 1 through 3. As in the pliers case, curved walls 20' and 30' are close to joint J' for the same reasons.

Figure 5:
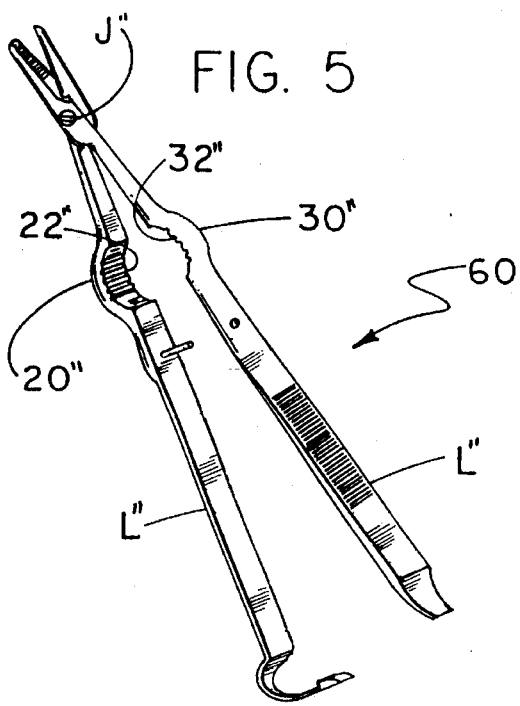
FIG. 5 is an isometric view of a pair of pliers with locking mechanism.

FIG. 5 shows a pair of pliers with locking mechanisms 60 for legs L" pivoting on J", with curved walls 20" and 30", also with the same design purposes in mind. Serrations 22" and 32", as previously described, provide additional friction. This will permit instrument 60 to lockingly maintain tubular member C in place until needle N is properly introduced in the former in a safe manner.

Figure 7:
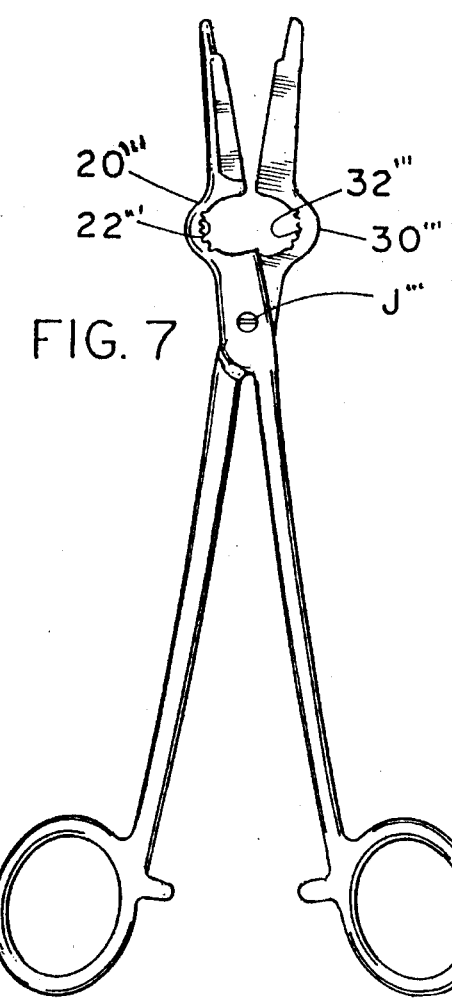
FIG. 7 shows a pair of specialized scissors with the curved portions opposite to the area where a user applies force to actuate the instrument.
Figure 6:
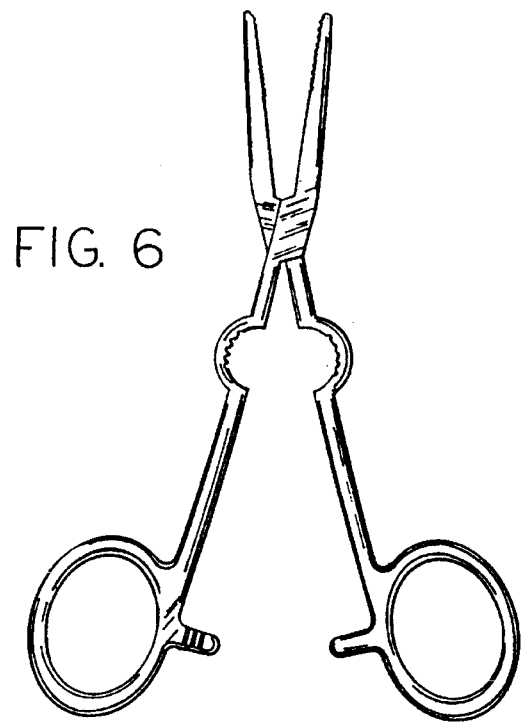
FIG. 6 is a top view of a another commonly used instrument for a dental or medical office.

Similarly, the instruments in FIGS. 6 and 7 show other instruments commonly used by dentists and physicians and that incorporate the present invention. As it can be seen from the instrument depicted in FIG. 7, curved walls 20'" and 30'", with serrations 22'" and 32'", can be formed on the portion of the leg members L in scissors that extend beyond joint J'" with similar results. In fact, the distance to the user's fingers is maximized in this instance thereby reducing the risk of accidental injury.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. In medical and dental instruments of the type that include a pair of movable elongated leg members joined by a joint about which said elongated leg members pivot, and a user actuates said elongated leg members by applying a force with his or her fingers, the improvement comprising a curved portion on each one of said elongated leg members and each of said curved portions having an internal concave wall cooperatively adapted to receive a tubular member thereby providing a firm grip on said tubular member, and said curved portions being located between the area where a user applies said force and said joint.

2. The improvement set forth in claim 1 wherein said tubular member is a container for housing needles thereby keeping said container at a minimum predetermined distance from a user's fingers.

3. The improvement set forth in claim 2 wherein said internal walls include friction enhancing irregularities.

* * * * *